United States Patent
Moheb

(10) Patent No.: US 12,076,115 B2
(45) Date of Patent: *Sep. 3, 2024

(54) SYSTEM AND METHOD FOR CLASSIFICATION OF DENTAL HEALTH BASED ON DIGITAL IMAGERY

(71) Applicant: Alireza Moheb, Concord, CA (US)

(72) Inventor: Alireza Moheb, Concord, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/133,679

(22) Filed: Apr. 12, 2023

(65) Prior Publication Data

US 2023/0248243 A1 Aug. 10, 2023

Related U.S. Application Data

(63) Continuation of application No. 16/815,738, filed on Mar. 11, 2020, now Pat. No. 11,653,838.

(51) Int. Cl.
*A61B 5/00* (2006.01)
*G06T 7/00* (2017.01)

(52) U.S. Cl.
CPC .......... *A61B 5/0088* (2013.01); *A61B 5/0071* (2013.01); *A61B 5/7264* (2013.01); *A61B 5/7267* (2013.01); *A61B 5/7275* (2013.01); *G06T 7/0012* (2013.01); *A61B 2576/02* (2013.01); *G06T 2207/10012* (2013.01); *G06T 2207/10024* (2013.01); *G06T 2207/10116* (2013.01); *G06T 2207/20084* (2013.01);
(Continued)

(58) Field of Classification Search
CPC ... A61B 5/0088; A61B 5/0071; A61B 5/7264; A61B 5/7267; A61B 5/7275; A61B 2576/02; A61B 5/0077; A61B 5/1032; A61B 5/682; G06T 7/0012; G06T 2207/10012; G06T 2207/10024; G06T 2207/10116; G06T 2207/20084; G06T 2207/30036; G06T 2207/30096; G06T 2207/10081; G06T 2207/20081; G06T 7/0014

See application file for complete search history.

(56) References Cited

U.S. PATENT DOCUMENTS

| | | | |
|---|---|---|---|
| 7,270,543 B2 * | 9/2007 | Stookey | A61B 1/247 433/29 |
| 8,647,119 B1 * | 2/2014 | Nagai | A61B 5/0088 433/29 |

(Continued)

OTHER PUBLICATIONS

Provisional Application Specification 62955321 (Year:2019).

*Primary Examiner* — Molly Wilburn
(74) *Attorney, Agent, or Firm* — KRAMER LEVIN NAFTALIS & FRANKEL LLP

(57) ABSTRACT

Systems for detecting and measuring certain dental defects and/or existing restorations, such as lesions which may or may not invade interproximal areas, using a neural network is disclosed. In some embodiments, a patient's health conditions and certain dental conditions such as crowding, presence of implants, gum disease, etc. are also considered by an automated system to classify the dental health of a patient into one or more risk classes. The system then suggests appropriate remedial measures and an appropriate maintenance program for that patient to keep therapy within guidelines of proven standard of care, leading the way to reduce tooth loss in population.

9 Claims, 15 Drawing Sheets

(52) U.S. Cl.
CPC .............. *G06T 2207/30036* (2013.01); *G06T 2207/30096* (2013.01)

(56) References Cited

U.S. PATENT DOCUMENTS

| | | | | |
|---|---|---|---|---|
| 8,768,016 | B2* | 7/2014 | Pan | A61B 5/0088 |
| | | | | 382/128 |
| 10,667,770 | B2* | 6/2020 | Myyrylainen | A61B 5/0086 |
| 11,653,838 | B2* | 5/2023 | Moheb | A61B 5/682 |
| | | | | 433/29 |
| 2004/0015327 | A1* | 1/2004 | Sachdeva | A61C 7/00 |
| | | | | 702/167 |
| 2005/0003323 | A1* | 1/2005 | Katsuda | A61B 1/00096 |
| | | | | 433/29 |
| 2007/0021670 | A1* | 1/2007 | Mandelis | A61B 5/0088 |
| | | | | 600/473 |
| 2007/0105069 | A1* | 5/2007 | Yamagishi | A61B 5/0088 |
| | | | | 433/29 |
| 2008/0063998 | A1* | 3/2008 | Liang | G01B 11/2441 |
| | | | | 433/29 |
| 2008/0170764 | A1* | 7/2008 | Burns | A61B 5/0088 |
| | | | | 382/128 |
| 2009/0185712 | A1* | 7/2009 | Wong | G06T 7/11 |
| | | | | 382/100 |
| 2016/0220200 | A1* | 8/2016 | Sandholm | A61B 5/0088 |
| 2018/0368694 | A1* | 12/2018 | Abrams | A61C 9/006 |
| 2019/0313963 | A1* | 10/2019 | Hillen | G06V 10/764 |
| 2019/0340760 | A1* | 11/2019 | Swank | G06T 7/74 |
| 2021/0201489 | A1* | 7/2021 | Ricci | G16H 70/60 |
| 2021/0338387 | A1* | 11/2021 | Inam | G06T 7/0012 |
| 2021/0343400 | A1* | 11/2021 | Inam | G16H 40/67 |
| 2022/0005588 | A1* | 1/2022 | Ricci | G16H 30/20 |
| 2022/0012815 | A1* | 1/2022 | Kearney | G16H 50/70 |

\* cited by examiner

| Risk factors | Low risk | High Risk (Stage I) | High Risk (Stage II) |
|---|---|---|---|
| 1. Interproximal invasion by restoration or disease | 1 | 2 | ≥ 3 |
| 2. Medical condition medication, or supplement causing low salivary flow or xerostomia* | No | No | Yes |
| 3. Tooth loss due to disease (not including third molar orthodontic or trauma related tooth loss) | 0 | 1 | ≥ 2 |
| 4. Orthodontics | No | Crowding | Malocclusion crowding |
| 5. Dental implants | 0 | 1 | ≥ 2 |
| 6. Daily sugar intake: soda, fruit juice, candy, chocolate sweetened drinks | No | No | Yes |
| 7. Life style: regular smoker, regular alcohol consumption or drug abuse | No | No | Yes |
| 8. Maintenance | 6-m maintenance; fluoride varnish; chlorohexidine | 4-mo maintenance; fluoride varnish; chlorohexidine | 3-mo maintenance; fluoride varnish; chlorohexidine |
| 9. Periodontal | Normal | Gingival inflammation | Bone loss recession |

| 10. Restoration options | 7. Chair side fillings good prognosis | 1. Chairs side filling guarded to poor prognosis. Lack of predictable contact, contour and smoothness | 1. Chair side filling material not recommended |
|---|---|---|---|
| | 2. Milled of lab made crown or onlay for defects wider than 1/3 of occlusal table | 2. Highly recommend milled or lab made products that can be polished smooth or glazed | 2. Milled or lab made products that can be polished smooth or glazed |
| | 3. Deep pit and grooves sealant or PRR recommended | 3. PRR on deep pit and grooves | 3. PRR on deep pit and grooves |
| | | | 4. Home care with Fluoride RX and Chlorohexidine RX products |

From Fig. 10A

SYSTEM AND METHOD FOR CLASSIFICATION OF DENTAL HEALTH BASED ON DIGITAL IMAGERY

CROSS-REFERENCE TO RELATED APPLICATIONS

This application is a continuation of U.S. patent application Ser. No. 16/815,738, filed on Mar. 11, 2020, the content of which is incorporated herein by reference in its entirety.

BACKGROUND

In the field of dentistry, diagnosis are performed generally by the General Dentists. However, since the act of diagnosis is done by a dentist alone, human judgment and error plays a major factor in diagnosis and remedial procedure needed. One factor contributing to such variance, is the fact that dimensions are small and observing a lesion with direct view visually or reading an x-ray is difficult. Also, the angel that the doctor is seeing the tooth surface from may limit the doctor's ability to see lesions. Furthermore, certain remedial procedures depend on location of a defect and/or it's proportionate size compared to the chewable surface of a tooth.

Proper and uniform diagnosis and remedial measures has been an ongoing challenge in this field. Some studies have shown 46% of patients are miss-diagnosed. This has become even more complicated, for example, in situations where more expert doctors oversee the work of newly graduates or when patient visiting multiple different dental office for different opinion. In some dental offices, experienced dentists continuously have to monitor the work of more junior dentists and explain to them the guidelines that they need to observe for diagnosis and appropriate remedial procedures. This process is inefficient, prone to error, and above all effecting success rate of patient care leading to tooth loss.

SUMMARY

Embodiments of this novel invention seek to address the problems described above by using a device that employs dental imagery of various form to measure certain critical dimensions related to various dental defects and conditions, and use such measurements to generate calculations such as percentage of loss of stiffness of tooth, and calculations that are not possible by a human due to the limitations of the human eye related to small dimensions, for example, stiffness reduction due to size of defect or restoration, bite force percentage and fracture risk level. Such measurements help to generate certain risk classifications that help the practitioners avoid misdiagnosis and treatment plan selection. In addition, such a device increases the speed and precision of measuring, which then increases the speed of diagnosis and treatment planning, and by extension will be helpful in increasing the success rate of a practice. Moreover, in education programs and or group clinical settings, this device will help reducing misdiagnosis from predoctoral students, and or junior doctors, and helps keep the junior doctors in line with the standard of care expected from them to increase efficiently and help them arrive at the proper diagnosis and the appropriate remedial measures that must follow. This increases the success rate, and at the same time, reduces the time patients spend in a dentist chair for diagnosis and treatment plan as a result of accurate and efficient calculations provided by such a device.

BRIEF DESCRIPTION OF THE FIGURES

FIGS. 10A-B shows several risk classification factors according to one embodiment.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

Figure 1:
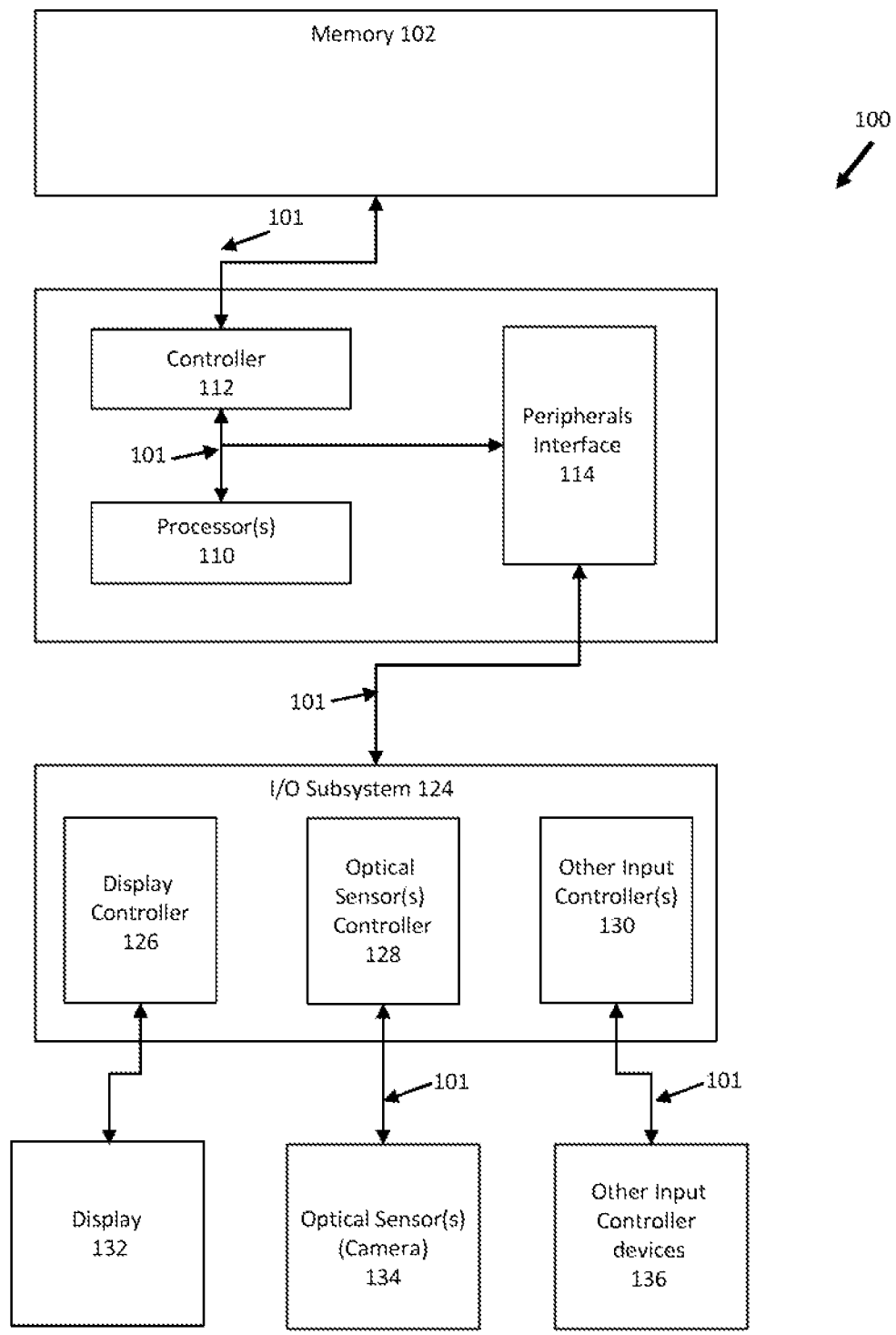
FIG. 1 illustrates a schematic of an exemplary system, according to one embodiment.

Attention is now directed towards embodiments of the device. FIG. 1 is a block diagrams illustrating computing devices 100 in accordance with some embodiments. The device 100 may include a memory 102 (which may include one or more computer readable storage mediums), a memory controller 112, one or more processing units (CPU's) 110, a peripherals interface 114, an input/output (I/O) subsystem 124, other input or control devices 130, optical sensor(s) controller 128, display controller 126, display system 132, optical sensor(s) (camera) 134 and other input control devices 136. These components may communicate over one or more communication buses or signal lines 101.

It will be understood by those skilled in the art and one or more parts or modules shows ad described with respect to FIG. 1 may be hosted in a cloud and communicate with the rest of the components of FIG. 1 remotely. Thus, FIG. 1 shows several components in close proximity for ease of explanations, but several of those components may be located remotely and communicate with the other components via a remote connection.

It should be appreciated that the device 100 is only one example of a device 100, and that the device 100 may have more or fewer components than shown, may combine two or more components, or a may have a different configuration or arrangement of the components. The various components shown in FIG. 1 may be implemented in hardware, software or a combination of both hardware and software, including one or more signal processing and/or application specific integrated circuits.

Memory 102 may include high-speed random access memory and may also include non-volatile memory, such as one or more magnetic disk storage devices, flash memory devices, or other nonvolatile solid-state memory devices. Access to memory 102 by other components of the device 100, such as the processor(s) 110 and the peripherals interface 114, may be controlled by the memory controller 112.

The peripherals interface 114 couples the input and output peripherals of the device to the processor(s) 110 and memory 102. The processors(s) 110 run or execute various software programs and/or sets of instructions stored in memory 102 to perform various functions for the device 100 and to process data.

The I/O subsystem 124 couples input/output peripherals on the device 100, such as the screen 132 and other input/control devices 136, to the peripherals interface 114. The I/O subsystem 124 may include a display controller 126 and one or more input controllers 130 for other input or control devices. The input controllers 160 may receive/send electrical signals from/to other input or control devices 136. The other input/control devices 136 may include physical buttons (e.g., push buttons, rocker buttons, etc.), dials, slider switches, joysticks, click wheels, and so forth. In some alternate embodiments, input controller(s) 130 may be coupled to any (or none) of the following: a keyboard, infrared port, USB port, and a pointer device such as a mouse.

The screen 132 may provide an input interface (in a case where the screen is a touch sensitive display) and an output interface between the device and a user. As explained above, the display controller 126 receives and/or sends electrical signals from/to the screen 132. The screen 132 displays visual output to the user. The visual output may include graphics, text, icons, video, and any combination thereof (collectively termed "graphics", "electronic content", and/or "electronic data").

The screen 132 may use LCD (liquid crystal display) technology, or LPD (light emitting polymer display) technology, although other display technologies may be used in other embodiments. The screen 132 and the display controller 126 may detect contact and any movement or breaking thereof using any of a plurality of touch sensing technologies now known or later developed, including but not limited to capacitive, resistive, infrared, fluorescence and surface acoustic wave technologies, as well as other proximity sensor arrays or other elements for determining one or more points of contact with a screen 132.

In some embodiments, Memory 102 may include other modules that store various other control logics such as an operating system, a communication module (or set of instructions), a contact/motion module (or set of instructions), a graphics module (or set of instructions), a text input module (or set of instructions), a Global Positioning System (GPS) module (or set of instructions), and applications (or set of instructions).

The operating system (e.g., Darwin, RTXC, LINUX, UNIX, OS X, WINDOWS, an embedded operating system such as VxWorks) includes various software components and/or drivers for controlling and managing general system tasks (e.g., memory management, storage device control, power management, etc.) and facilitates communication between various hardware and software components.

The Optical sensor 134 may be in form of a hand-held camera. In the context on the present invention, such camera may be in a shape/form that can be inserted in an oral cavity to take imagery from inside of a mouth. In one embodiment, instead of or in addition to an optical sensor, a 3D scanner may be used which can produce a 3-dimensional model of the tooth. In one embodiment, a CBCT (Cone Beam Computed Tomography) may be used which is a specialized type of dental Computed Tomography (vs medical CT) that provides more information than conventional dental X-rays. The scan from CBCT may be used to generate a 3-dimensional model of a tooth, teeth, jaw tissue and bone It will be apparent to those skilled in the art that any combination of devices and imaging technologies may be used individually or in concert to ascertain certain needed information about a tooth, teeth or jaw and its condition required for diagnosis and treatment planning.

Several embodiments of the invention will now be described. For sake of readability, specific references to the hardware components of the device 100 will be omitted. However, those skilled in the art understand the various functions described below are performed by various components of device 100.

Figure 2:
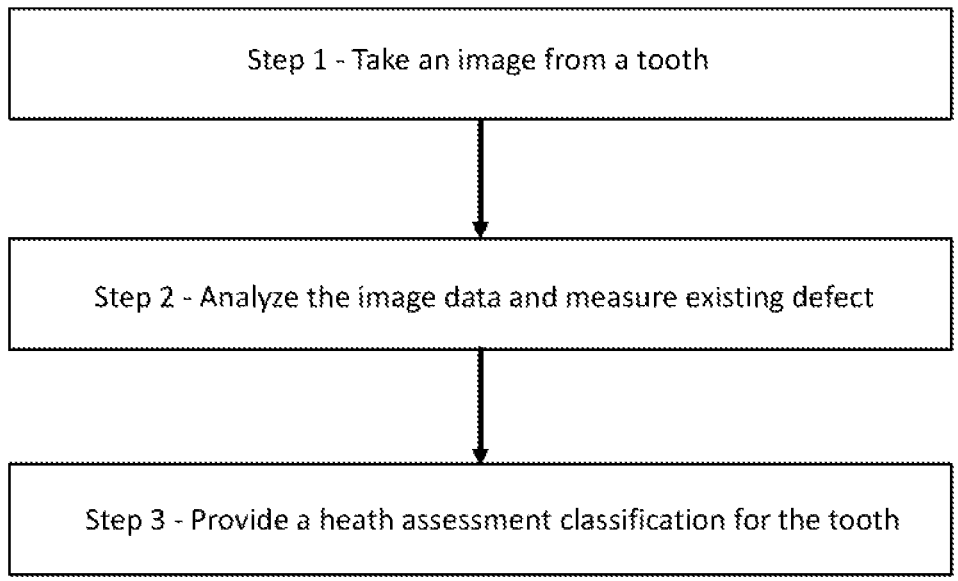
FIG. 2 illustrates a flowchart that shows the process of using the system, according to one embodiment.

FIG. 2 illustrates the general steps that are taken using the device shown in FIG. 1 to provide a health assessment of a tooth. First, in step 1, a dentist or dentists auxiliary uses a camera or scanner (for example camera 134) to take one or more images of a tooth. In step 2, the images are analyzed based on several criteria, and as a result a health assessment is provided in step 3 as a result of the analysis. Before elaborating on methodologies for analyzing the images, we will first explain the criteria that results in various classifications.

Presence of cavities in certain areas of the tooth presents more challenges for diagnosis and restoration. In addition, interproximal invasion elevates the risk level by a higher degree since it directly affects the structural integrity of a tooth and periodontium (gums and bone) destruction. The Interproximal areas of teeth are highly prone to decay, partly due to the fact that proper cleaning of interproximal areas are difficult. In addition, a patient's medical condition, diet, salivary flow are contributing factors to the health of the teeth. To better understand what type of defects on the teeth classifies the teeth condition as high or low risk, several examples are provided in FIGS. 3-9.

Figure 3:
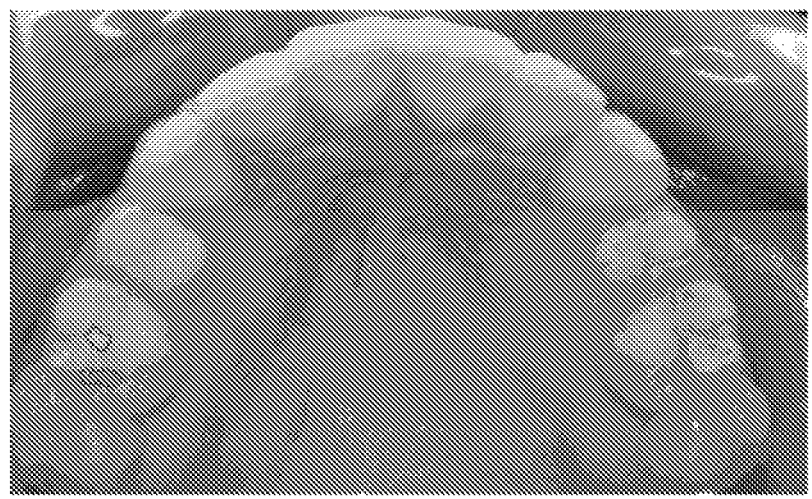
FIG. 3 shown an image of several teeth two of which have defects.

FIG. 3 is a color image of bottom teeth of a patient. The blue areas indicate existing fillings which are small. The red area marks one new lesion. In this case, the small lesion can be filled and as a result this patient and the his/her tooth are low risk.

Figure 4:
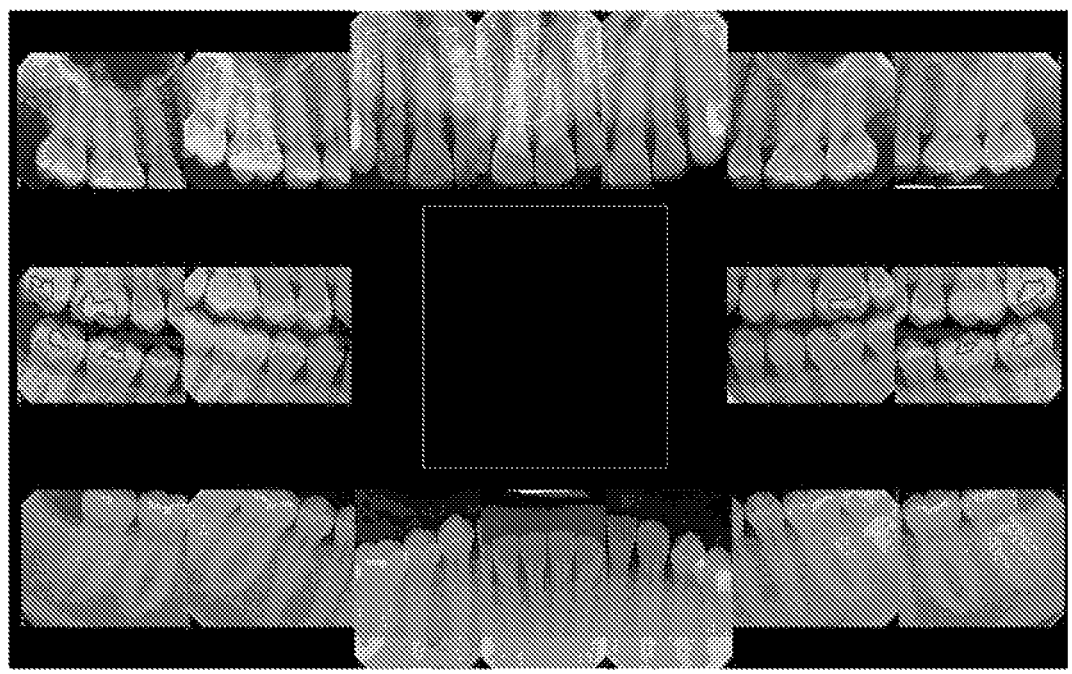
FIG. 4 shows a x-ray images of a mouth that includes few defects.

FIG. 4 show an x-ray of full mouth of another patient. The blue marks indicate existing fillings that are in the middle of teeth and not in interproximal areas. This is another example of a low risk case.

Figure 5:
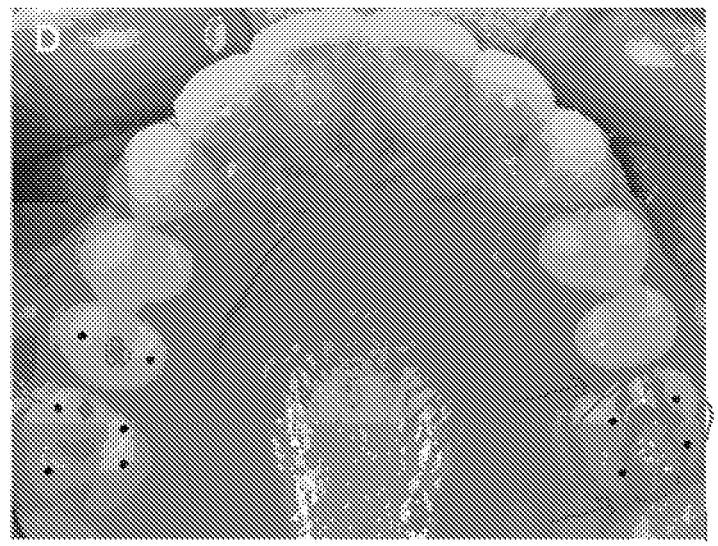
FIG. 5 shows an image of several teeth with some defects.
Figure 6:
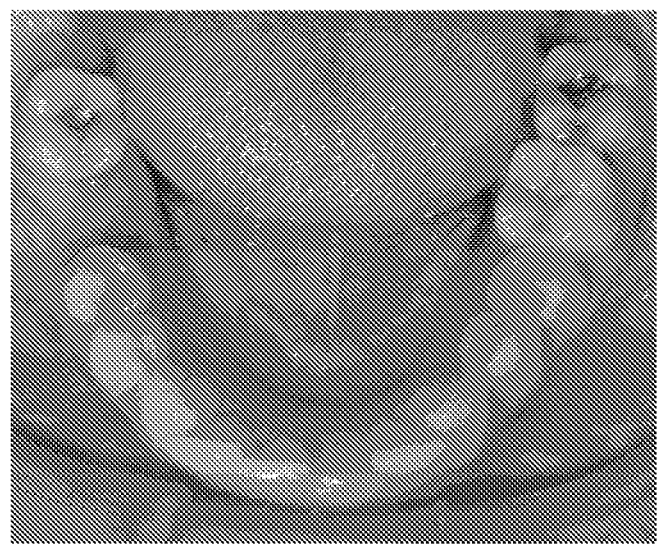
FIG. 6 shows an image of several teeth with one tooth missing.

FIG. 5 shows another example of color image of top of (chewing surface) teeth of a patient. In this example, the arrows point to two interproximal involvement by restoration. Because of the number of interproximal involvement (more than 1), this patient is classified as High Risk stage I. The proper treatment, based on size and calculation of force on that tooth that is measured by the device, is a lab made smooth hygienic partial or full coverage crown for the tooth with interproximal involvement. Furthermore, the marked areas on the left side of the mouth indicate new lesions.

Since the surface areas of these lesions is less than ⅓ of the total chewable surface area of the tooth, these teeth can be restored with filling.

Figure 7:
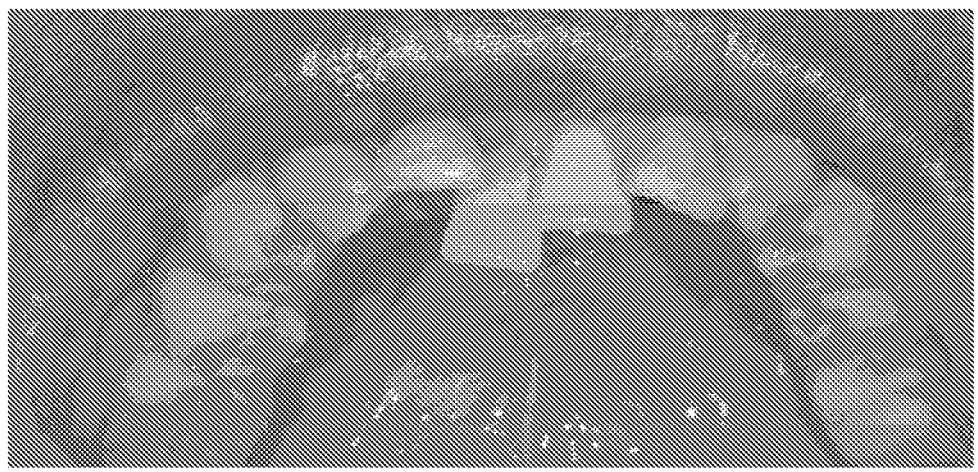
FIG. 7 shows an image of several teeth with crowding.
Figure 8:
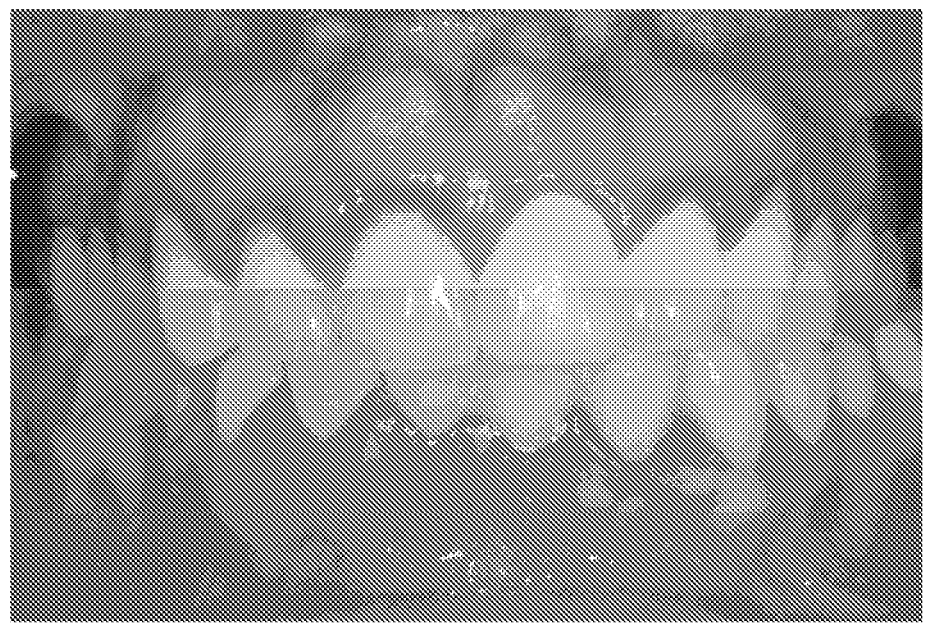
FIG. 8 shows an image of a mouth with gum disease.
Figure 9:
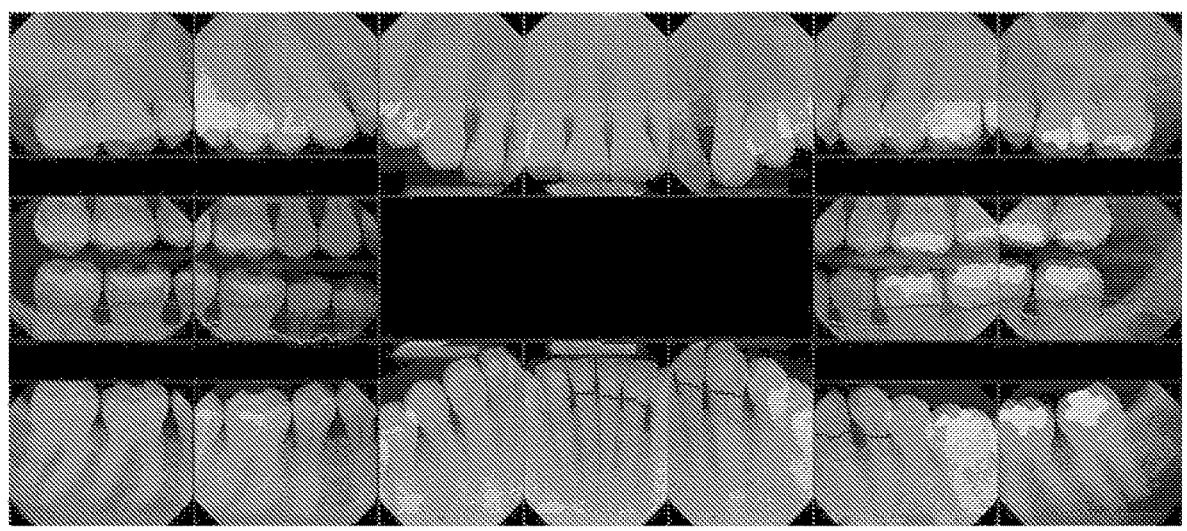
FIG. 9 shows an x-ray image of a mouth with bone loss.

FIGS. 7-9 show other conditions that can contribute to risk factor. For example, FIG. 7 shows overcrowding of front teeth. FIG. 8 shows gingival inflammation (the red areas show inflammation), this condition also known as Gingivitis also contribute to risk factor. FIG. 9 is an x-ray that illustrates the issue of bone loss. The upper line drawn across the teeth is where the bone needs to be and the line below it is where the bone level is in this case. This patient has bone loss and this also contributes to risk factor.

The above examples illustrate several cases where a dentist makes an observation, evaluates the patient's condition and makes a diagnosis and prescribes remedial procedures to address the patient's needs. This process however is prone to human error and varying degree of deviance. This is partially due to the fact that in cases where there is interproximal invasion and or the size of lesions or existing restoration is more than ⅓ of the chewing surface area of a tooth, restoration by filling is not proper as the structural integrity of the tooth can be compromised. In these situations, a partial or full coverage crown is an ideal remedial action. However, since the lesions may be small and few of them may be present on a tooth, it is hard to measure them with naked eye and/or determine just by looking whether they amount to ⅓ or more of the chewable surface area of the tooth, and force of bite in a specific tooth will need more precise calculation of dimension in micrometer which is impossible for human eye. Furthermore, the depth of the filling is another metric that determines the risk level. If the depth of the filling is more a pretrimmed range, which may be 30% to 50% of the clinical crown, then the tooth is classified as high risk and a crown or onlay may be needed.

In addition, given that several conditions such as health of the gums, overcrowding and bone loss make further complicate the diagnosis, it is not uncommon for two dentists to suggest different remedial procedures for the same conditions due to miscalculation and not considering all factors necessary all at once, sometimes because of limited time available at that moment to consider all factors for a proper diagnosis and therapy selection.

As mentioned earlier, this issue is particularly problematic in education program and junior dentist and in an office where more than one dentists practices, so the novel embodiments of the invention aide a dentists to arrive at a proper diagnosis by detecting interproximal invasions, measuring the size of the lesions, determining if the size of the lesions amount to ⅓ of the chewable surface area, depth of lesion or restoration and also take into account other relevant factors such as health of the gums, overcrowding and bone loss. An automated evaluation system that can conduct accurate measurement of the lesions take into account various relevant risk factors can help with determining whether increased frequency of preventive care is needed, which can help avoid premature loss of teeth.

The automated risk classification of the present can classify a tooth, teeth, gums, bite, crowding of the teeth of the patient, and by extensions his/her oral health conditions, into three risk levels or if new classification are defined in the field, then more than three risk classifications. These risk levels encourage the patients to take responsibility for their oral health and also allows a dentist to better manage the patients' care by prescribing the appropriate treatment, maintenance frequency and preventative treatments.

For example, patients with three or more interproximal invasions may be classified as high risk stage II. Such a classification require a 3-month maintenance schedule. Patients with two interproximal invasions may be classified as high risk stage I. Such a classification may require a 4-month maintenance visits. And patients with one interproximal invasion may be classified as low risk. In this case, a 6-months maintenance schedule is proper. This system can define treatment protocols but also provide standards for communications between practitioners. These classifications and remedial selection may be adjusted to the most current guidelines suggested by the latest research at any time.

FIGS. 10A and 10B shows a chart that includes a number of risk factors and risk classifications according to one embodiment of the invention. As shown in FIGS. 10A and 10B, presence of interproximal invasion by restoration or disease can classify the oral health of a patient into three risk stages two of which are considered high risk if the patient has more than two interproximal invasion and one is considered low risk if the patient has one interproximal invasion. Also, if the patient is taking medications or supplements that cause low salivary flow, the oral health of that patient can be classified as high risk. Generally, medications taken for the following conditions may cause oral complications: allergies, hypertension, obesity, depression, psychotic disorders, anxiety, acne, epilepsy, pain management, nausea, cancer chemotherapy, birth control and several others.

Furthermore, several health conditions may classify the patient as high risk. For example, the following medical conditions can cause oral complications: diabetes, heart disease, cancer, obesity, immune deficiency, Alzheimer disease, anemia, cystic fibrosis, rheumatoid arthritis, stroke, mumps, Parkinson disease, surgical removal of salivary glands, and dehydration.

As shown in FIGS. 10A and 10B, medical conditions, medication and supplements can classify the patient's oral health as high risk. Tooth loss due to disease may also classify as high risk. FIGS. 10A and 10B proposes different class of high risk (stage I or stage II) based on whether there is crowding or malocclusion crowding. Presence of dental implants is also a risk factor. The chart in FIGS. 10A and 10B suggests that one implant classifies as high risk stage I and more than two implants classifies as high risk stage II. Lifestyle and dietary intake can also play an important role. As shown in FIGS. 10A and 10B, depending on the risk classification, a different maintenance schedule and/or restoration options is prescribed to improve success rate by proven evidence of most current research.

As mentioned earlier, automation of the process by which the classifications similar to one illustrated in FIGS. 10A and 10B, results in increased efficiency and less chance of error and a uniform approach by a group of dentists. Such operation requires detection of lesions and interproximal invasion as well as measuring their size. In addition, other factors such as presence of implant, overcrowding and gum disease can be detected by a machine or observed by a dentists and entered into a system along with other relevant risk factors such as medical conditions and medications so that a system can output a risk classification.

Several methodologies for detection and measurement of lesions and interproximal invasions will now be described. In one embodiment, a neural network can be trained to detect presence of lesions and interproximal invasions.

Figure 11A:
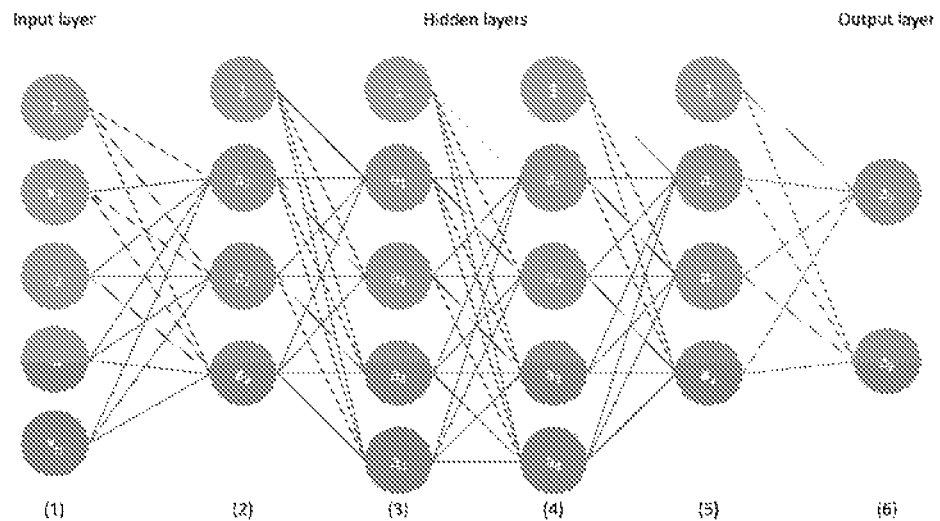
FIG. 11a shows a schematic of a neural network according to one embodiment.
Figure 11B:
FIG. 11b shows a block diagram of a neural network according to ne embodiment.

Attention is now directed to FIGS. 11a and 11b showing a high-level illustration of a convolutional neural network (CNN, or NN for short). In the field of Artificial Intelligence, such networks are used for analysis and classification of images. Generally, a NN is "trained" by gathering and classifying a series of samples (training data), the NN is then put through a process of digesting the samples for each classification. Once a NN is trained, it can be fed an input, if the input has similarity within a degree to any of the sample data that was used during the training process, the NN then "classifies" the input and outputs a classification result. In the context of imagery analysis, for example, if a NN is trained to classify between images of cats and dogs, first, during the training process, a series of cat images in various positions, lighting situation and physical variations are put into a training set labeled as "cat". A similar process is done for a series of images of dogs.

The NN then processes the samples and at the end "learns" to associate images of cats as cats and images of dogs as dogs. This "classification" works based on the assumption that the image that is inputted to the NN resembles to some extent any of the sample images that was originally used to train the NN. During the training process, the NN forms a series of "layers" also called "hidden layers" which record a series of characteristics of the sample training data. As the input is fed into the NN, the image goes through these layers and each time various aspect of the image is analyzed by the NN and at the end a determination is made as to whether the image could be classified as any of the labels that the NN is trained to identify. FIG. 11b shows the CNN showing in FIG. 11a as three main components of input 201, classification 202 which is meant to encapsulate all the layers of the CNN and the output 203.

The actual inner workings of a CNN has more intricacies and complexities, however, the provided description is sufficient for those skilled in the art to appreciate the novel approach that will be explained in the present application to detect the presence of interproximal invasions and lesions. In a training process a series of images showing interproximal invasions and lesions fed into a CNN for training, each of the series of images are labeled during the training process. The number and quality of images used for training a NN is important. Given that lesions and interproximal invasions can occur on any part of a tooth, a vast number of training samples from various angles should be gathered and labeled. The training process for interproximal invasions and lesions should also be separate since the goal is to detect each separately. Thereafter when an image of a tooth is fed into a CNN, if the CNN is able to classify those images as having either interproximal invasion or lesions or not.

In addition, since more one of interproximal invasion may be present on one tooth, the NN needs to be carefully trained to learn that more than one of these may be present. In that case, the output can also include a number of each occurrence. The output of a NN also includes a percentage in terms of degree of certainty of classification of the image. The NN outputs a percentage possibility that the image that it processed belong to a classification that it has been trained to detect. This degree of certainty can then be used to evaluate whether the output of the NN may need further examination or a threshold can be established below which the results are not accepted.

Figure 12:
FIG. 12 shows an image of a tooth with some defect.

During the training process, the images of tooth with lesions or interproximal invasions need to be annotated similar to FIG. 12. Annotated training images allow the NN to understand what a lesion or interproximal invasion looks like on an image. From such annotation the NN learns what to look for in an input. In this case, the color contrast signifies an area of a tooth that is not normal, and when a proper number of annotated images are used for training the NN, the NN will be able to mark input images that show lesions or interproximal invasions.

Figure 13A:
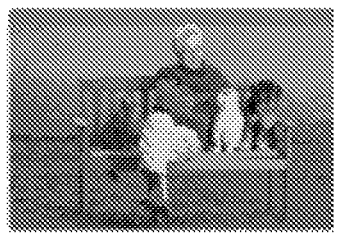
FIGS. 13a-13c show the process of detection and segmentation on an image, according to one embodiment.
Figure 13B:
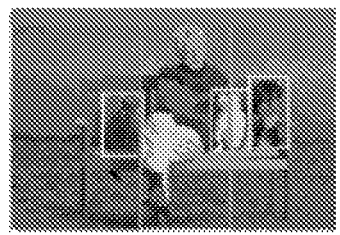
Figure 13C:
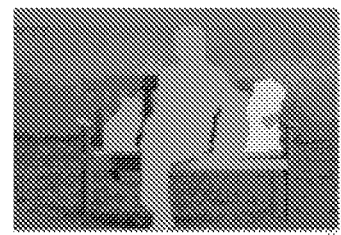

As part of detection of lesions and interproximal invasions, an output of a convolutional neural network needs to go through segmentation to isolate the perimeter of the lesion or the interproximal invasion for measurement. Image segmentation involves dividing a visual input into segments to simplify image analysis. Segments represent objects or parts of objects, and comprise sets of pixels. FIGS. 13a-13c illustrate the process of classification, detection and segmentation. In FIG. 13a, we have three class of objects which are a person, cats and one dog. In FIG. 13b, these "objects" are detected a box is drawn around them. In FIG. 13c the image is segmented based on the detected objects. In the context of the present invention, a classification is done on a tooth, and then if there are lesions or interproximal invasions they will be detected and then they are segmented. Once the detected objects, which in this context will be lesions and interproximal invasions, are segmented, we can measure them.

Figure 14:
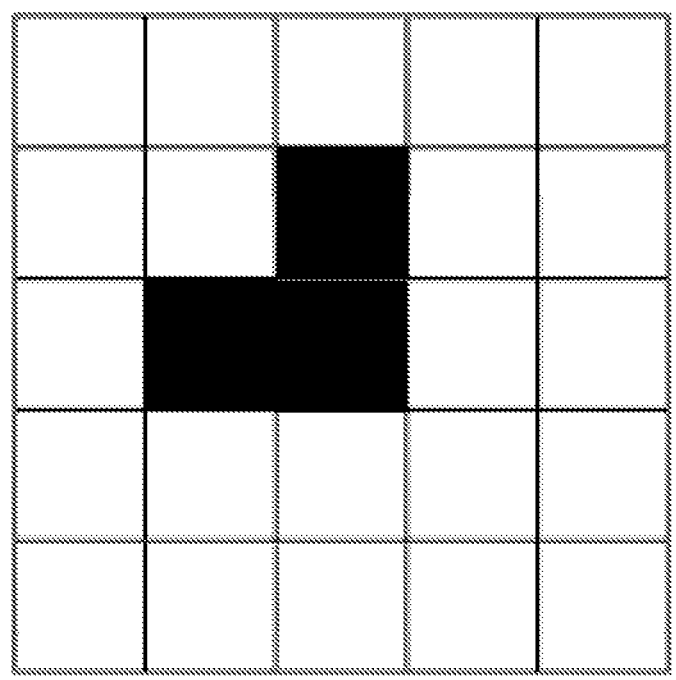
FIG. 14 shows a sample of few pixels of an image according to one embodiment.

FIG. 14 shows a 5×5 grid where three squares are marked black. If we want to measure the size of the three black squares relative to the grid, we would divide the number of black squares which is three by the total number of squares which is twenty and we arrive at 15%. Assume the that we can count the total number of pixels that represent the surface area of a tooth. After detection and segmentation of a lesion or interproximal invasion, we can count the number of pixels occupied by those and understand the relative measurement of the lesions or the interproximal invasion compared to the total surface area of the tooth. It will be understood by those skilled in the art that FIG. 14 represent one example of how an area within an image can be measured. There are other techniques that can be employed for measurement of a segmented object within an image.

In one embodiment, another methodology to detect the presence of interproximal invasions and lesions may be to utilize florescent lighting. Fluorescence is one of a number of processes by which materials can emit light after appropriate activation. A key feature of fluorescence is that the emission of light matches the mode of excitation, so if the light is pulsed in a particular way, the same pattern will be seen in the fluorescence emissions. When light is absorbed into a fluorophore, the molecule becomes electronically excited to higher energy levels, from where decay to lower energy levels occurs by emitting radiation and thermal relaxation. The intensity of the emission is linearly proportional to the concentration of the fluorophore present in the target.

In this embodiment, when an image of a tooth is captured, the interproximal invasion and lesion will have a different color and shade making them distinguishable from the other part of the tooth. Then the image can be scanned to isolate the areas with different color shade and those areas can be marked as lesions or interproximal invasion depending on their location.

In one embodiment, a hand-held 3D scanner may be used to produce a volumetric model of the teeth. Such scanner combined with florescence may be used to detect and mark the lesions and interproximal invasions. One type of volumetric modeling of teeth has been described in application number WO2018022940A1, entitled "Intraoral scanner with dental diagnostics capabilities." In addition, penetration imaging techniques may be used to detect the presence of areas with different densities (i.e. lesions, cracks, and interproximal invasions).

In another embodiment, a neural network (NN) can be trained to detect the presence of interproximal invasions and lesions from x-ray images. In this embodiment, a training set of x-ray images can be gathered that show interproximal invasion and another set can be gathered that show different types of lesions. The NN can be trained by the training set to detect the presence of lesions and interproximal invasions. To achieve a greater degree of accuracy two NN that work with digital color images and x-ray images can be employed in parallel and the result can be compared to avoid miss-classification by either of the NN.

Figure 15:
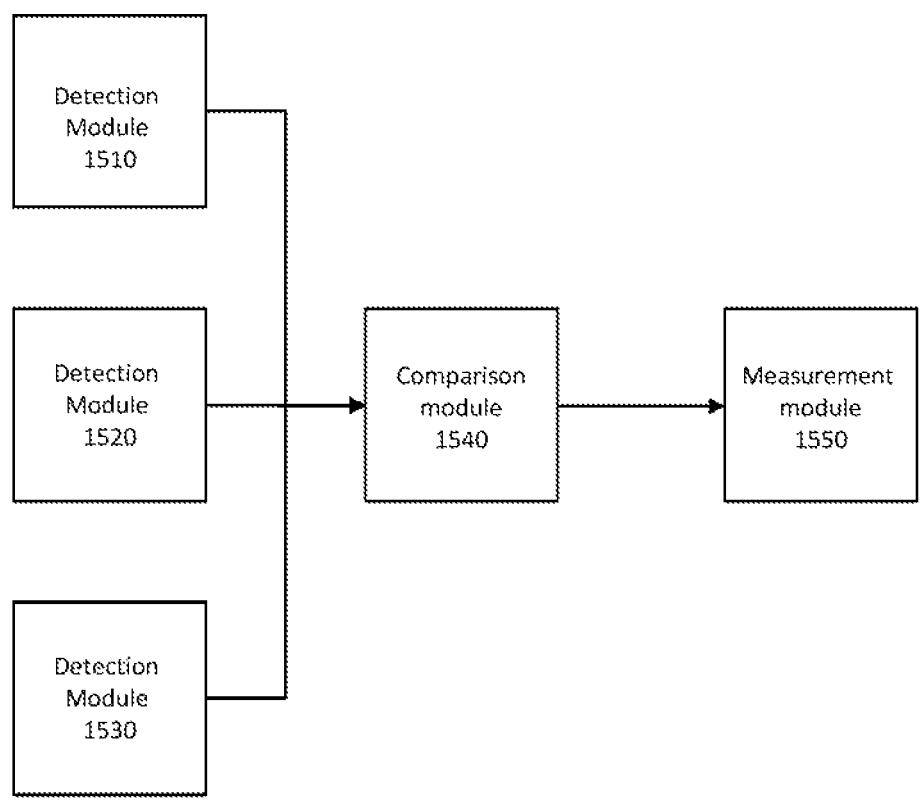
FIG. 15 shows a block diagram of several modules that compare the result of various detection module, according to one embodiment.

FIG. 15 shows an embodiment where more than one detection techniques are used to detect the presence of interproximal invasions and lesions. In this example, detection module 1510 may be a NN trained for detection on color images, detection module 1520 may be a NN trained for detection on x-ray images and detection module 1530 may be detecting interproximal invasions and lesions using florescent light. As shown in FIG. 15 the output of these modules are analyzed by comparison module 1540. Comparison module 1540 may then compare the output of each of the detection modules to decrease the chance of erroneous detection or false positive. Once the results are checked, an image that is appropriate for measurement by the measurement module 1550 is then used to determine the size of the lesions and/or interproximal invasions.

Figure 16:
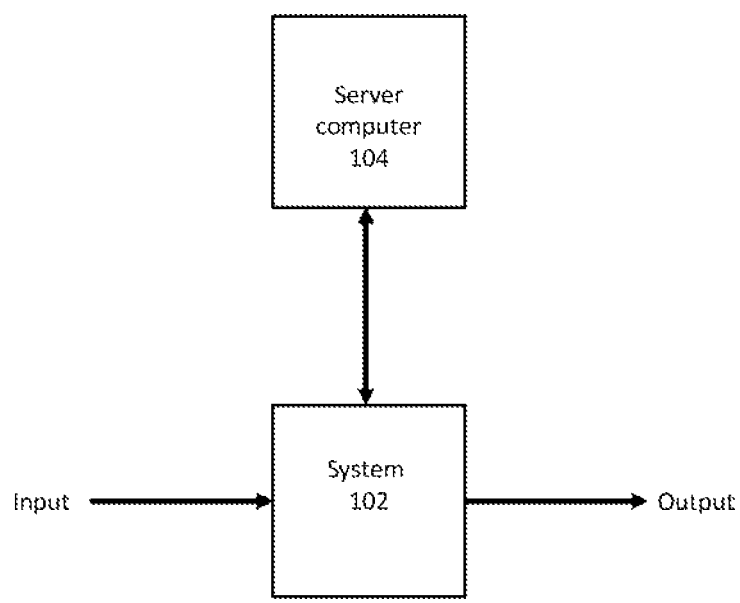
FIG. 16 shows a block diagram of a system communicating with a remote server according to one embodiment.

Referring back to FIG. 1, the elements of FIG. 15 may be stored on memory 102 and the processor 110 can run the NN. In one embodiment, one or more NN and other elements of FIG. 15 may be based on a remote server computer and the system shown in FIG. 1 may communicate with a remote server computer. This is shown in FIG. 16, where system 102 (which is shown in detail in FIG. 1) receives an input and it communicates with the server computer 104, and provides an output. In this "cloud based" approach the Artificial Intelligence (i.e. the Neural Network) is hosted on a remote computer that can receive the data and analyze the image and return the results.

In one embodiment, other issues such as overcrowding, presence of implants and bone loss, even though can be observed by a dentist and considered as part of a risk classification protocol similar to what is illustrated in FIGS. 10A and 10B, can be automated for efficiency. In one embodiment, an output of a handheld camera that is used to take images of the teeth and then used for detection of lesions or interproximal invasions may also be used to detect missing tooth, implants, crowding and bone loss.

Figure 17:
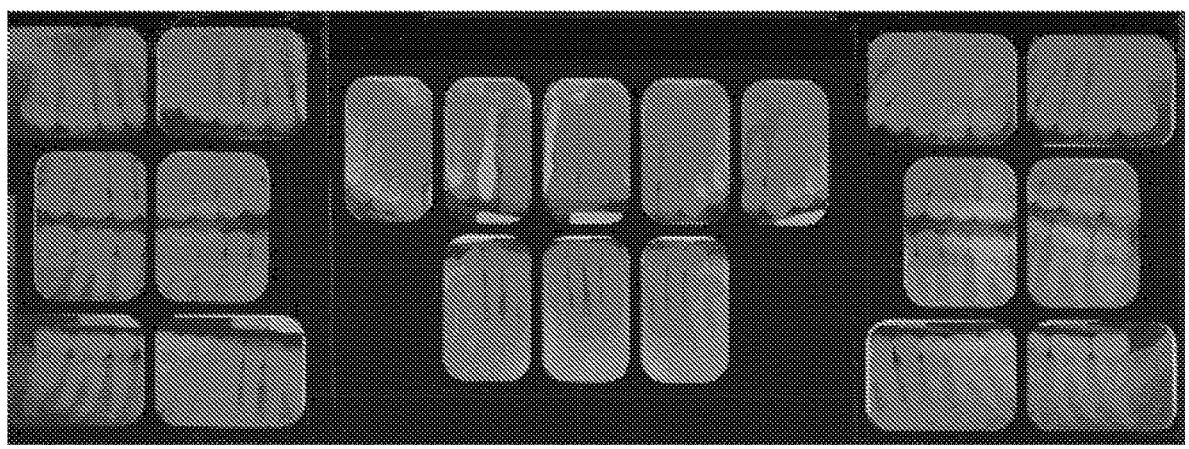
FIG. 17 shows a x-ray image of a mouth showing a few implants.

Implants and bone loss may also be detected from x-ray or CBCT (cone beam) images. FIG. 17 shows an x-ray image that include a couple of teeth having implant roots. A NN, for example, can be trained to detect implants in an x-ray. Then the system can account for the number of implants and reflect that in the risk classification. Furthermore, as shown in FIG. 9 bone loss can also be detected from x-ray images. A NN can be trained to detect whether there is bone loss as shown in FIG. 9. Crowding can also be detected from x-ray images and/or digital color images, which can be a 3D scanner in one embodiment, that can be captured using a handheld camera for intraoral photography.

It will be understood that the novel embodiments of the invention provide several advantages: a system for detecting various issues such as lesions can be used in combination with a software that considers issues such as health conditions, medications and lifestyle to classify a patent's risk and recommend proper restorative actions and/or maintenance program. Such a system brings about increased efficiency in a dental practice which in turn saves a considerable amount of cost and overhead, especially where more senior dentists need to evaluate the work on more junior dentists.

Such a system is also tremendously helpful in communicating with the patient. Since the system takes into account present issues such as lesions, crowding, etc. and also takes into account health condition, medication and lifestyle of the patient, communication of why the patient falls under certain risk classification, and what in terms of remedial measures and maintenance program is required, is much easier to determine and communicate with the patient. Furthermore, this system can be used to show patients the impact of their lifestyle, current state of their oral health and medication they take has on their life and its associated cost. And it can be simulated for the patient that when their lifestyle choice become healthier and their current state of oral health improves, their cost of maintenance can be lowered. This system also helps patients understand the urgency of a patient's condition and what will happen if they delay proper care needed to improve their oral health. Therefore, this system has an important use in educating the patients about their oral health.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, methods and processes described herein can be included in hardware modules or apparatus. These modules or apparatus may include, but are not limited to, an application-specific integrated circuit (ASIC) chip, a field-programmable gate array (FPGA), a dedicated or shared processor that executes a particular software module or a piece of code at a particular time, and/or other programmable-logic devices now known or later developed. When the hardware modules or apparatus are activated, they perform the methods and processes included within them.

What is claimed is:

1. A device for assessing health of a tooth, the device comprising:
   a processor;
   an optical sensor or 3D scanner coupled to the processor and configured to be inserted in an oral cavity and capture one or more digital color images of a tooth from inside the oral cavity, and
   a computer readable medium coupled to the processor and configured to store executable control logic, the control logic configured to:
   input the one or more digital color images in a first neural network trained to classify a predetermined set of dental conditions and to classify the one or more digital color images based on the predetermined set of dental conditions,
   input one or more Computed Tomography (CT) scan(s) or Cone Beam Computed Tomography (CBCT) scan(s) of the tooth in a second neural network trained to classify the predetermined set of dental conditions, wherein the second neural network classifies the one or more CT or CBCT scans of the tooth, generate a treatment plan or restorative action for the tooth based on the classification results from the first neural network and the second neural network; and wherein the first neural network classifies the one or more images based on the ratio of a first area of the tooth having lesions and a second area of the tooth being the chewable surface of the tooth which is inclusive of the first area, and wherein when the first area is more than ⅓ of the second area, the tooth is classified as high risk.

2. The device of claim 1, wherein the first neural network is configured to implement a degree of variance in the classification based on additional external information comprising specific medical history, specific habit and diet.

3. The device of claim 1, wherein the second neural network classifies the one or more CT or CBCT scans based on the ratio between an area of the tooth that show sign of restoration and an area of the tooth that is intact without decay.

4. The device of claim 1, wherein the treatment plan or restorative action for the tooth is based on type of restoration on the tooth, size of the restoration, and dimensions of the restoration.

5. The device of claim 1, wherein the treatment plan or restorative action includes an amount of restoration material needed to fill one or more cavities.

6. A system comprising:
a processor;
an optical sensor or 3D scanner coupled to the processor and configured to be inserted in an oral cavity and capture one or more digital color images of a tooth from inside the oral cavity, and
a computer readable medium coupled to the processor and configured to store executable control logic, the control logic configured to:
input the one or more digital color images in a first neural network trained to classify a predetermined set of dental conditions and to classify the one or more digital color images based on the predetermined set of dental conditions,
input one or more Computed Tomography (CT) scan(s) or Cone Beam Computed Tomography (CBCT) scan(s) of the tooth in a second neural network trained to classify the predetermined set of dental conditions, wherein the second neural network classifies the one or more CT or CBCT scans of the tooth; and
generate a treatment plan or restorative action for the tooth based on the classification results from the first neural network and the second neural network, wherein the first neural network is configured to implement a degree of variance in the classification based on additional external information comprising specific medical history, specific habit and diet.

7. A system comprising:
a processor;
an optical sensor or 3D scanner coupled to the processor and configured to be inserted in an oral cavity and capture one or more digital color images of a tooth from inside the oral cavity, and
a computer readable medium coupled to the processor and configured to store executable control logic, the control logic configured to:
input the one or more digital color images in a first neural network trained to classify a predetermined set of dental conditions and to classify the one or more digital color images based on the predetermined set of dental conditions,
input one or more Computed Tomography (CT) scan(s) or Cone Beam Computed Tomography (CBCT) scan(s) of the tooth in a second neural network trained to classify the predetermined set of dental conditions, wherein the second neural network classifies the one or more CT or CBCT scans of the tooth; and
generate a treatment plan or restorative action for the tooth based on the classification results from the first neural network and the second neural network, wherein the second neural network classifies the one or more CT or CBCT scans based on the ratio between an area of the tooth that show sign of restoration and an area of the tooth that is intact without decay.

8. A system comprising:
a processor;
an optical sensor or 3D scanner coupled to the processor and configured to be inserted in an oral cavity and capture one or more digital color images of a tooth from inside the oral cavity, and
a computer readable medium coupled to the processor and configured to store executable control logic, the control logic configured to:
input the one or more digital color images in a first neural network trained to classify a predetermined set of dental conditions and to classify the one or more digital color images based on the predetermined set of dental conditions,
input one or more Computed Tomography (CT) scan(s) or Cone Beam Computed Tomography (CBCT) scan(s) of the tooth in a second neural network trained to classify the predetermined set of dental conditions, wherein the second neural network classifies the one or more CT or CBCT scans of the tooth; and
generate a treatment plan or restorative action for the tooth based on the classification results from the first neural network and the second neural network, wherein the treatment plan or restorative action for the tooth is based on type of restoration on the tooth, size of the restoration, and dimensions of the restoration.

9. A system comprising:
a processor;
an optical sensor or 3D scanner coupled to the processor and configured to be inserted in an oral cavity and capture one or more digital color images of a tooth from inside the oral cavity, and
a computer readable medium coupled to the processor and configured to store executable control logic, the control logic configured to:
input the one or more digital color images in a first neural network trained to classify a predetermined set of dental conditions and to classify the one or more digital color images based on the predetermined set of dental conditions,
input one or more Computed Tomography (CT) scan(s) or Cone Beam Computed Tomography (CBCT) scan(s) of the tooth in a second neural network trained to classify the predetermined set of dental conditions, wherein the second neural network classifies the one or more CT or CBCT scans of the tooth; and
generate a treatment plan or restorative action for the tooth based on the classification results from the first neural network and the second neural network, wherein the treatment plan or restorative action includes an amount of restoration material needed to fill one or more cavities.

* * * * *